United States Patent [19]
Bowden et al.

[11] Patent Number: 5,663,370
[45] Date of Patent: Sep. 2, 1997

[54] CHEMICAL INTERMEDIATES USEFUL IN AGRICULTURE

[75] Inventors: Martin Charles Bowden, Rastrick; Stephen Martin Brown, Upper Cumberworth, both of United Kingdom

[73] Assignee: Zeneca Limited, London, England

[21] Appl. No.: 687,547

[22] PCT Filed: Mar. 8, 1995

[86] PCT No.: PCT/GB95/00500

§ 371 Date: Aug. 8, 1996

§ 102(e) Date: Aug. 8, 1996

[87] PCT Pub. No.: WO95/25729

PCT Pub. Date: Sep. 28, 1995

[30] Foreign Application Priority Data

Mar. 21, 1994 [GB] United Kingdom .................. 9405492

[51] Int. Cl.$^6$ ...................... C07D 311/76; C07C 69/76
[52] U.S. Cl. .............................................. 549/290; 560/60
[58] Field of Search ................................. 549/290; 560/60

[56] References Cited

FOREIGN PATENT DOCUMENTS

| | | |
|---|---|---|
| 0 178 826 | 4/1986 | European Pat. Off. . |
| 0 278 595 | 8/1988 | European Pat. Off. . |
| 0 370 629 | 5/1990 | European Pat. Off. . |
| 0 414 153 | 2/1991 | European Pat. Off. . |
| 0 460 575 | 12/1991 | European Pat. Off. . |
| 0 583 589 | 2/1994 | European Pat. Off. . |
| 1137466 | 12/1968 | United Kingdom . |
| 90/07493 | 7/1990 | WIPO . |
| 92/08703 | 5/1992 | WIPO . |
| 92/18494 | 10/1992 | WIPO . |
| 92/18487 | 10/1992 | WIPO . |
| 93/16986 | 9/1993 | WIPO . |
| 94/08968 | 4/1995 | WIPO . |

OTHER PUBLICATIONS

Barbier, M., "Synthesis of Substituted 2-Phenyl αβ-Unsaturated Aliphatic Acids", *Synthetic Communications*, vol. 19 (9&10), pp. 1661–1667 (1989).

Black, Gerald G., "The Synthesis and Flash Vacuum Pyrolysis of 4-Alkenylisochroman-3-Ones", *Journal of Chemical Research, Synopses.*, vol. 9, Sep. 1986,. pp. 332–333.

Kosuge, Takuo et al., "Synthesis and Some Reactions of 6-Bromooxindole", *Chem. Pharm. Bull.*, vol. 33 (1985), pp. 1414–1418.

Elix, J. A. et al., "Annelated Furans, XIII. Methylation of 3-Acylbenzofuran-2(3H)-Ones", *Aus. J. Chem.*, vol. 26 (1973), pp. 1079–1091.

Hutchings, Michael G., "The Regio-and Stereochemistry of the Alkoxide-Induced Ring-Opening of Methoxymethylidene-Substituted Homophthalic Anhydride", *Tetrahedron*, vol. 44 (1988), No. 12, pp. 3727–3734.

Wolfbeis, Otto S., "Uber die Umalgerung von Alkoxymethylen-und Amino-methylenhomophthalsaureanhydriden zu Isocumarinen bzw. Isochinolinonen", *Liebigs Ann. Chem.*, (1981), pp. 819–827.

*Primary Examiner*—Amelia Owens
*Attorney, Agent, or Firm*—Joseph R. Snyder; Marian T. Thomson

[57] ABSTRACT

Intermediates of formula (I),

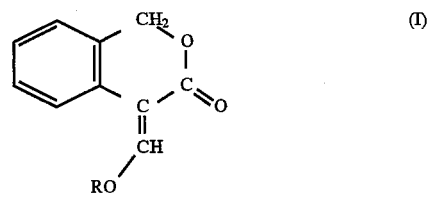

wherein R is H or $CH_3$; processes for preparing them and their use as chemical intermediates, especially for preparing fungicidal acrylic ester derivatives.

10 Claims, No Drawings

CHEMICAL INTERMEDIATES USEFUL IN AGRICULTURE

The present invention provides chemical compounds which are useful as intermediates for the preparation of agrochemicals (especially fungicides), to processes for preparing said chemical compounds and to methods of using them to prepare other intermediates.

The compounds of the invention can be used to prepare fungicidal acrylic ester derivatives, for example those known from EP-178826, EP-370629, EP-414153, EP-460575, WOg3/16986, WO92/18494, WO90/07493, EP-586393 or WO94/08968.

The present invention provides a compound of formula (I), wherein R is hydrogen or methyl; or a compound of formula (Ia) wherein M is an alkali metal or alkaline earth metal cation and n is 1 or 2.

It is preferred that M is an alkali metal (especially sodium or potassium).

In one aspect present invention provides a process for the preparation of a compound of formula (I), wherein R is methyl, the process comprising reacting isochromanone with trimethyl orthoformate in the presence of an acid anhydride.

In another aspect the present invention provides a process for the preparation of a compound of formula (I), wherein R is hydrogen, the process comprising reacting a compound obtainable by treating isochromanone with a source of methoxide anions, with an alkyl formate and acidifying the product so formed.

In a further aspect the present invention provides a process for the preparation of a compound of formula (I), wherein R is hydrogen, the process comprising the steps:

(a) reacting isochromanone with a source of methoxide anions; and, (b) reacting the product of step (a) with an alkyl formate and acidifying the product so formed.

In a still further aspect the present invention provides a process for the preparation of a compound of formula (I), wherein R is methyl, the process comprising reacting a compound obtainable by treating a compound of formula (I), wherein R is hydrogen, with a suitable base, with a suitable methylating agent.

In another aspect the present invention provides a process for the preparation of a compound of formula (I), wherein R is methyl, the process comprising the steps:

(a) reacting a compound of formula (I), wherein R is hydrogen, with a suitable base; and, (b) reacting the product of step (a) with a suitable methylating agent.

In yet another aspect the present invention provides a process for the preparation of a compound of formula (I), wherein R is methyl, the process comprising the steps:

(a) reacting a compound obtainable by treating isochromanone with a source of methoxide anions, with an alkyl formate and acidifying the product so formed;

(b) reacting the product of step (a) with a suitable base; and, (c) reacting the product of step (b) with a suitable methylating agent.

In a further aspect the present invention provides a process for the preparation of a compound of formula (I), wherein R is methyl, the process comprising the steps:

(a) reacting isochromanone with a source of methoxide anions;

(b) reacting the product of step (a) with an alkyl formate and acidifying the product so formed;

(c) reacting the product of step (b) with a suitable base; and (d) reacting the product of step (c) with a suitable methylating agent.

In a still further aspect the present invention provides a process for the preparation of a compound of formula (II), wherein X is chlorine or bromine, the process comprising reacting a compound of formula (I), wherein R is methyl, with a thionyl halide of formula $SOX_2$ (wherein X is as previously defined) and reacting the product so formed with methanol.

In another aspect the present invention provides a process for the preparation of a compound of formula (II), wherein X is chlorine or bromine, the process comprising the steps:

(a) reacting a compound obtainable by treating a compound of formula of formula (I) (wherein R is hydrogen) with a suitable base, with a suitable methylating agent; and, (b) reacting the product of step (a) with a thionyl halide of formula $SOX_2$ (wherein X is as previously defined) and reacting the product so formed with methanol.

In yet another aspect the present invention provides a process for the preparation of a compound of formula (II), wherein X is chlorine or bromine, the process comprising the steps:

(a) reacting a compound of formula (I), wherein R is hydrogen, with a suitable base;

(b) reacting the product of step (a) with a suitable methylating reagent; and, (c) reacting the product of step (b) with a thionyl halide of formula $SOX_2$ (wherein X is as previously defined) and reacting the product so formed with methanol.

In a further aspect the present invention provides a process for the preparation of a compound of formula (II), wherein X is chlorine or bromine, the process comprising the steps:

(a) reacting a compound obtainable by treating isochromamone with a source of methoxide anions, with an alkyl formate and acidifying the product so formed;

(b) reacting the product of step (a) with a suitable base;

(c) reacting the product of step (b) with a methylating agent; and, (d) reacting the product of step (c) with a thionyl halide of formula $SOX_2$ (wherein X is as previously defined) and reacting the product so formed with methanol.

In a still further aspect the present invention provides a process for the preparation of a compound of formula (II), wherein X is chlorine or bromine, the process comprising the steps:

(a) reacting isochromamone with a source of methoxide anions;

(b) reacting the product of step (a) with an alkyl formate and acidifying the product so formed;

(c) reacting the product of step (b) with a suitable base;

(d) reacting the product of step (c) with a methylating agent; and, (e) reacting the product of step (d) with a thionyl halide of formula $SOX_2$ (wherein X is as previously defined) and reacting the product so formed with methanol.

In another aspect the present invention provides a process for the preparation of a compound of formula (I), wherein R is methyl, the process comprising the steps:

(a) reacting isochromanone with a source of methoxide anions;

(b) reacting the product of step (a) with an alkyl formate; and, (c) reacting the product of step (b) with a methylating agent.

In yet another aspect the present invention provides a process for the preparation of a compound of formula (II), wherein X is Chlorine or bromine, the process comprising the steps:

(a) reacting isochromanone with a source of methoxide anions;

(b) reacting the product of step (a) with an alkyl formate;

(c) reacting the product of step (b) with a methylating agent; and (d) reacting the product of step (c) with a thionyl halide of formula $SOX_2$ (wherein X is as previously defined) and reacting the product so formed with methanol.

It is preferred that X is chlorine.

Scheme 1 shows the processes of the present invention in pictorial fashion.

A compound of formula (I), wherein R is methyl, can be prepared by reacting isochromanone with trimethyl orthoformate in the presence of an acid anhydride (preferably an alkyl acid anhydride [wherein alkyl preferably contains from 1–6, especially 1–4, carbon atoms in a straight or branched chain], such as acetic anhydride or iso-butyric anhydride), optionally in a solvent (such as the alkyl acid anhydride or trimethyl orthoformate or a mixture of the two and/or optionally an inert solvent, for example a hydrocarbon solvent (such as toluene or a xylene)), at a suitable temperature (preferably in the range 20°–250° C., especially 50°–200° C., for example 90°–150° C.), and at a suitable pressure in the range 0.1–10 atmospheres, such as atmospheric or autogenic pressure.

A compound of formula (I), wherein R is hydrogen, can be prepared by reacting isochromanone with a source of methoxide anions (for example from an alkali metal methoxide or an alkaline earth metal methoxide, for example sodium, potassium, calcium or magnesium methoxide) and reacting the product so formed with an alkyl formate and then acidifying the reaction mixture with a suitable acid (preferably a mineral acid, such as hydrochloric acid). It is preferred that this preparation is conducted in the presence of a solvent (preferably present by way of an excess of alkyl formate or, alternatively, an ether, for example tetrahydrofuran) and at a suitable temperature (such as in the range –30° C. to 50° C., for example –20° C. to 30° C.). It is preferred that the source of methoxide anions is from sodium methoxide and it is further preferred that the sodium methoxide is freshly prepared.

An alkyl formate is preferably a $C_{1-4}$ alkyl formate, for example methyl formate, ethyl formate, n-propyl formate, iso-propyl formate, n-butyl formate or tert-butyl formate. It is preferred that the alkyl formate is methyl formate.

A compound of formula (I), wherein R is methyl, can be prepared by treating a compound of formula (I), wherein R is hydrogen, with a suitable base (such as an alkaline earth or alkali metal hydroxide, bicarbonate or carbonate, for example sodium hydroxide, sodium bicarbonate or potassium carbonate), and reacting the product so formed with a suitable methylating agent (such as dimethyl sulphate or methyl iodide). It is preferred that the preparation is carried out in a solvent (such as a polar solvent, for example N,N-dimethylformamide). It is preferred that the methylation step is carried out in the temperature range –30° C. to 90° C., such as –30° C. to 30° C., especially –10° C. to 10° C.

Alternatively, a compound of formula (I), wherein R is methyl, can be prepared by treating a compound of formula (I), wherein R is hydrogen, with methanol in the presence of a strong acid (such as sulphuric or hydrochloric acid), optionally in a suitable solvent (such as methanol itself) and at a suitable temperature (such as 10° C. to 70° C., especially the boiling point of methanol).

Alternatively, a compound of formula (I), wherein R is methyl, can be prepared by reacting isochromanone with a source of methoxide anions (as defined above), reacting the product so formed with an alkyl formate (as defined above) and then treating the product formed with a suitable methylating agent (as defined above). It is preferred that this preparation is conducted in a suitable solvent (such as a polar solvent, for example N,N-dimethylformamide) and in the temperature range –30° C. to 90° C., such as –10° C. to 50° C., especially 0° C. to 40° C.

A compound of formula (II), wherein X is chlorine or bromine, can be prepared by reacting a compound of formula (I), wherein R is methyl, with a thionyl halide of formula $SOX_2$ (wherein X is as previously defined), optionally in the presence of a solvent (preferably present by way of a excess of thionyl halide or, alternatively, a polar solvent such as N,N-dimethylformamide) and reacting the product so formed with methanol. The preparation is carried out at a suitable temperature, preferably in the range 10°–150° C., such as at the boiling point of the thionyl halide. It is preferred that this reaction is carried out in at least a small amount of N,N-dimethylformamide.

The following Examples illustrate the invention. Where shown, infrared (IR) and nuclear magnetic resonance (NMR) data are selective; no attempt has been made to list every absorption. The following abbreviations are used throughout:

ppm=parts per million s=singlet
d=doublet m=multiplet
GCMS=gas chromatography/mass spectroscopy
THF=tetrahydrofuran
DMF=N,N-dimethylformamide

EXAMPLE 1

Step 1

To a solution of 3-isochromanone (Compound (A) in Scheme 1) (6.35 g, 42.9 mmol) in dry tetrahydrofuran (70 ml) under nitrogen at 0° C. was added sodium methoxide (4.63 g, 85.8 mmol) causing a slight rise in temperature. The mixture was recooled to 0° C. and methyl formate (5.1 g, 85.8 mmol) added over 10 minutes at this temperature. Once the addition was complete stirring was continued at 0° C. for 10 minutes before the solution was allowed to warm to room temperature (21° C.) whereupon it began to thicken and evolve carbon monoxide. More tetrahydrofuran (50 ml) was added and stirring increased. After 3.5 hours additional sodium methoxide and methyl formate (2 mol equalvalents of each) were charged to the reaction vessel at 0° C. and the reaction once more allowed to warm to room temperature. After 22 hours analysis indicated that the reaction had ceased. The reaction mass was quenched into ice cold water (200 ml), acidified to Congo Red using concentrated hydrochloric acid (18 ml) and the organic phase separated. The aqueous phase was extracted with dichloromethane (3×180 ml), the organics combined, water washed (2×100 ml), dried over anhydrous sodium sulphate and concentrated in vacuo to yield 4-(α-hydroxy)methylene-2H-chromen-3(4H)-one (ie Compound (B) in Scheme 1)) (6.985g, 80%) as a brown/beige solid.

(m/z): 176 (M$^+$), 158, 130, 119, 102, 77, 63, 51.
NMR (CDCl$_3$): 12.4 (d,1H); 7.8 (d,1H); 7.35–7.0 (m,4H); 5.3 (s,2H) ppm.

Step 2

The product of Step 1 (3.03 g, 17.22 mmol) was dissolved in dry N,N-dimethylformamide (50 ml) with stirring under nitrogen. Potassium carbonate (3.56 g, 25.79 mmol) was added and the brown solution cooled to 2° C. whereupon dimethyl sulphate (1.63, 17.14 mmol) was added dropwise over 10 minutes whilst maintaining the temperature below 4° C. Once the addition was complete the reaction was stirred for 30 minutes at 4° C. prior to being allowed to warm to room temperature. After 2 hours the reaction mass was quenched into water (50 ml). The organic phase was separated and the aqueous phase extracted with diethyl ether (3×50 ml). The organics were combined, water washed (2×50 ml), dried and concentrated in vacuo to yield 4-(α-methoxy)methylene-2H-chromen-3(4H)-one (ie Compound C in Scheme 1) (3 g, 85%) as a beige solid (containing a small amount of DMF).
(m/z): 190(M$^+$), 175, 161, 147, 118, 115, 103, 89, 63, 51, 39.
NMR (CDCl$_3$): 7.9 (d,1H); 7.75 (s,1H); 7.4–7.1 (m,3H); 5.3 (s,2H); 4.0 (s,3H) ppm.

Step 3

Thionyl chloride (8.115 g, 68.5 mmol) was added dropwise to the product of Step 2 (0.5 g, 2.63 mmol) at room temperature. The solution so formed was boiled under reflux (approximately 75° C.) for 4 hours and then allowed to stand overnight at room temperature. Excess thionyl chloride was removed by distillation prior to the dropwise addition of methanol (5 ml) at room temperature. Once addition was complete the reaction mass was boiled under reflux for a further 1.5 hours. After this time methanol was removed on the rotary evaporator to yield E-methyl 2-(chloromethyl) phenyl-3-methoxy-propenoate (0.458 g, 72%) as a yellow gum.
(m/z): 242 ND 240 (M$^+$), 210, 208, 196, 176, 149, 129, 115, 75.
NMR (CDCl$_3$): 7.6 (s,1H); 7.5–7.0 (m,4H); (s,2H); 3.75 (s,3H); 3.6 (s,3H) ppm.
IR $v_{max}$ (thin film): 3000, 1750, 1700, 1630, 1440 cm$^{-1}$.

EXAMPLE 2

Isochromanone (3.3 mol, 1 mol equivalent), trimethyl orthoformate (8 mol equivalent) and acetic anhydride (2 mol equivalent) were agitated at 100° C. for 48 hours, and then at 110° C. for 8 hours. GCMS analysis of the reaction mixture 3-Isochromanone (11) (0.52 g, 3.3 mmol), trimethyl orthoformate (0.71 g, 6.6 mmol) and acetic anhydride (2.78 g, 26 mmol) were heated at 100° C. for 48 hours and then at 110° C. for 8 hours. GCMS analysis of the reaction mixture showed 4-(α-methoxy)methylene-2H-chromen-3 (4H)-one (ie Compound C in Scheme 1) to be present as a minor component.

EXAMPLE 3

Isochromanone (0.52 g, 3.3 mmol), trimethyl orthoformate (0.71 g, 6.6 mmol) and acetic anhydride (2.78 g, 26 mmol) were heated at 100° C. for 48 hours and then at 110° C. for 8 hours. GCMS analysis of the reaction mass showed 4-(α-methoxy)methylene-2H-chromen-3(4H)-one (ie Compound C in Scheme 1) to be present as a minor component.

EXAMPLE 4

Isochromanone (2.0 g) was charged to a dry 100 ml flask, with THF (14 ml) under a nitrogen atmosphere. The solution was cooled to 5° C., sodium methoxide (1.6 g) was added quickly and the mixture was cooled back to 5° C. Methyl formate (1.62 g) was added and the mixture was stirred at 0°14 5° C. for 90 minutes after which time further THF (2 ml) was added. The reaction mixture was stirred at ambient temperature overnight. Water (14 ml) was added and the reaction mixture was acidified to congo red with concentrated hydrochloric acid. The aqueous was extracted with dichloromethane (3×25 ml). The combined extracts were dried over magnesium sulphate, then the solvent removed to leave 4-(α-hydroxy)methylene-2H-chromen-3(4H)-one as a beige solid (1.9 g).

EXAMPLE 5

Isochromanone (2.0 g) was charged to a dry 100 ml flask, with methyl formate (14 ml) under a nitrogen atmosphere. The solution was cooled to 5° C. and sodium methoxide (1.6 g) was added whilst maintaining the temperature below 8° C. The reaction mixture was stirred at 0°–5° C. for 70 minutes then at ambient temperature overnight. Water (14 ml) was added and the resulting mixture was acidified to congo red with concentrated hydrochloric acid. A precipitate formed which was filtered at ambient temperature, washed with water (5 ml), and dried in a vacuum desiccator to give 4-(α-hydroxy)methylene-2H-chromen-3(4H)-one (2.0 g).

EXAMPLE 6

4-(α-Hydroxy)methylene-2H-chromen-3(4H)-one (6.8 g) was charged to a 250 ml flask with DMF (100 ml) and cooled to 10° C. Potassium carbonate (8.5 g) and dimethylsulphate (4.8 g) were added sequentially and the mixture stirred at 10° C. for 3 hours. Water (100 ml) was added and the aqueous mixture was extracted with dichloromethane (3×100 ml). The extracts were combined, washed with water (2×100 ml), dried over magnesium sulphate and the solvent removed under vacuum to give 4-(α-methoxy)methylene-2H-chromen-3(4H)-one as a brown solid (7.0 g).

When this reaction was repeated a pale oil was obtained after solvent removal. Crystallisation from petroleum ether 80°–100° C. gave 4-(α-methoxy)methylene-2H-chromen-3 (4H)-one as yellow needles (melting point 97° C.).

EXAMPLE 7

4-(α-Methoxy)methylene-2H-chromen-3(4H)-one (1.9 g containing circa 2% DMF) was charged to a 50 ml flask and blanketed with nitrogen. Freshly redistilled thionyl chloride (31.2 g) was added and the mixture was heated to reflux for 6 hours. Excess thionyl chloride was removed by atmospheric distillation and final traces of thionyl chloride were removed by applying vacuum. The reaction mixture was cooled to 0° C. and methanol (15.0 g) was added carefully. The resulting mixture was heated to reflux for 1 hour and stirred at ambient temperature overnight. Excess methanol was removed under vacuum to leave an orange oil. Trituration with hexane produced E-methyl 2-(chloromethyl) phenyl-3-methoxypropenoate as a yellow waxy solid (1.7 g).

EXAMPLE 8

4-(α-Methoxy)methylene-2H-chromen-3(4H)-one (4 g, containing approximately 2% DMF) was added to thionyl chloride (65.2 g) with stirring. The reaction mixture was refluxed for 1 hour after which time excess thionyl chloride was removed by distillation. The residue was cooled to 5° C. and methanol (39.0 g) added. The reaction mixture was stirred overnight at room temperature and then refluxed for 1 hour. Methanol was removed under reduced pressure to leave a residue. E-methyl 2-(chloromethyl)phenyl-3-methoxypropenoate (1.26 g) was obtained by crystallisation using cyclohexane:ethyl acetate 9:1.

EXAMPLE 9

This preparation of compound C (Scheme 1) goes via the sodium salt of anion (D) (Scheme 1).

Isochromanone (2.0 g) was dissolved in DMF (15 ml) and the resulting solution was stirred and cooled to 5° C. under nitrogen. Sodium methoxide (1.5 g) was added and, after cooling the mixture back to 5° C., methyl formate (1.6 g) was added. The reaction mixture was allowed to warm gradually to 15° C. and stirred at this temperature for 5 hours. The reaction mixture was cooled to 5° C., dimethyl sulphate (1.9 g) added, and the resulting mixture was allowed to gradually warm to room temperature and was stirred over a weekend. Water (25 ml) was then added and, after stirring for 1 hour, the mixture was extracted with dichloromethane (4×25 ml). The organic extracts were combined, washed with water, dried and evaporated under reduced pressure to leave a residue which was redissolved in dichloromethane. The organic solution was washed with water, dried and evaporated to leave a liquid.

Petroleum ether 80°–100° C. was added to the liquid and the mixture was heated. The petroleum ether solution was decanted off while hot, and when cool, 4-(α-methoxy)methylene-2H-chromen-3(4H)-one (0.5 g) crystallised out of solution.

CHEMICAL FORMULAE
(In Description)

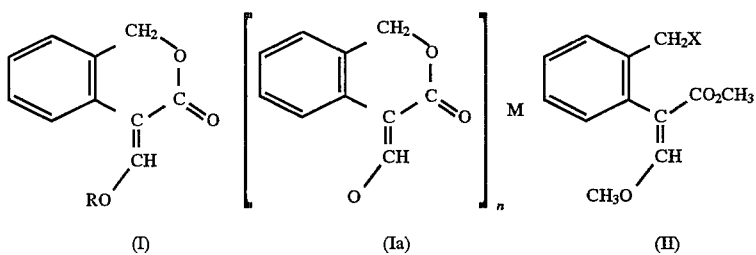

Scheme 1

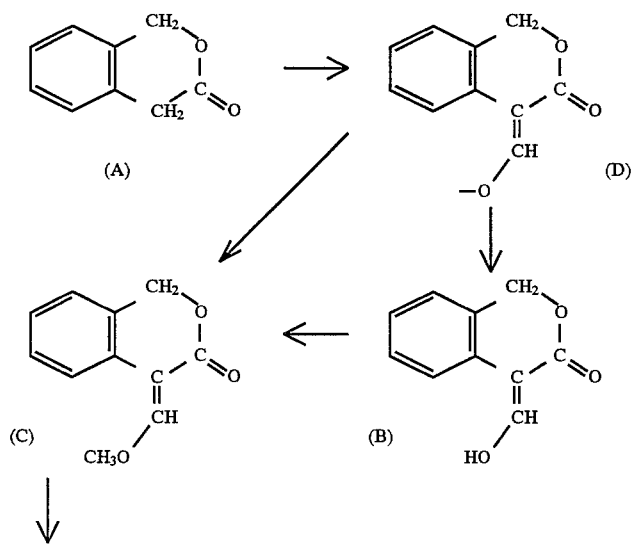

-continued
CHEMICAL FORMULAE
(In Description)

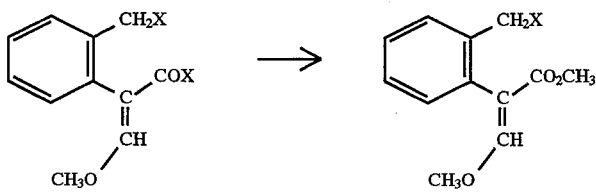

We claim:

1. A compound of formula (I) or (Ia):

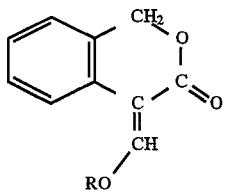   (I)

wherein R is hydrogen or methyl; or

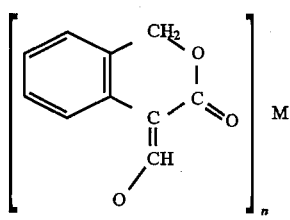   (Ia)

wherein M is an alkali metal or alkaline earth metal cation and n is 1 or 2.

2. A process for the preparation of a compound of formula (I):

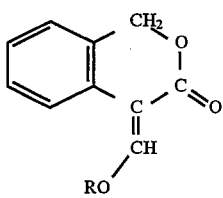   (I)

wherein R is methyl, the process comprising reacting isochromanone with trimethyl orthoformate in the presence of an acid anhydride.

3. A process for the preparation of a compound of formula (I):

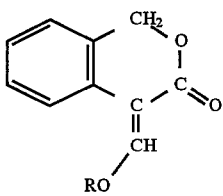   (I)

wherein R is hydrogen, the process comprising reacting a compound obtainable by treating isochromanone with a source of methoxide anions, with an alkyl formate and acidifying the product so formed.

4. A process as claimed in claim 3 the process comprising the steps:

(a) reacting isochromanone with a source of methoxide anions; and, (b) reacting the product of step (a) with an alkyl formate and acidifying the product so formed.

5. A process for the preparation of a compound of formula (I):

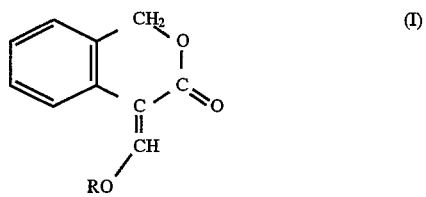   (I)

wherein R is methyl, the process comprising reacting a compound obtainable by treating a compound of formula (I):

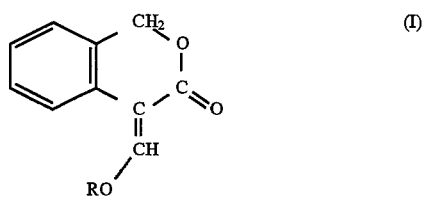   (I)

wherein R is hydrogen, with a suitable base, with a methylating agent.

6. A process as claimed in claim 5, the process comprising the steps:

(a) reacting a compound of formula (I), wherein R is hydrogen, with a suitable base; and, (b) reacting the product of step (a) with a suitable methylating agent.

7. A process as claimed in claim 6, the process comprising the steps:

(a) reacting isochromanone with a source of methoxide anions;

(b) reacting the product of step (a) with an alkyl formate and acidifying the product so formed;

(c) reacting the product of step (b) with a suitable base; and (d) reacting the product of step (c) with a suitable methylating agent.

8. A process for the preparation of a compound of formula (I):

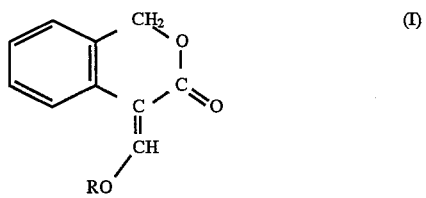   (I)

wherein R is methyl, the process comprising the steps:

(a) reacting isochromanone with a source of methoxide anions;

(b) reacting the product of step (a) with an alkyl formate; and, (c) reacting the product of step (b) with a methylating agent.

9. A process for the preparation of a compound of formula (II):

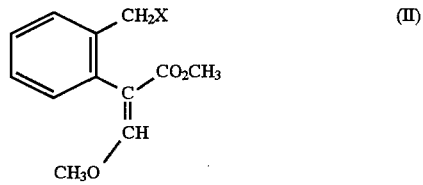

wherein X is chlorine or bromine, the process comprising reacting a compound of formula (I):

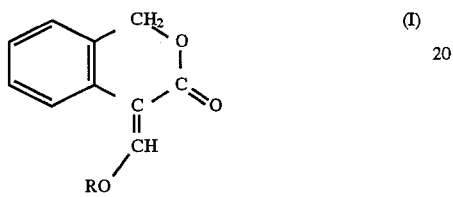

wherein R is methyl, with a thionyl halide of formula $SOX_2$, wherein X is as previously defined, and reacting the product so formed with methanol.

10. A process for preparing a compound of formula (II):

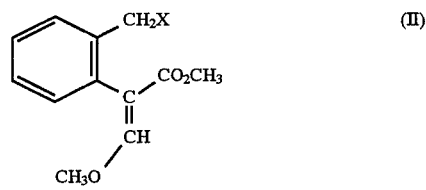

wherein X is chlorine or bromine, the process comprising the steps:

(a) reacting isochromanone with a source of methoxide anions;

(b) reacting the product of step (a) with an alkyl formate;

(c) reacting the product of step (b) with a methylating agent; and (d) reacting the product of step (c) with a thionyl halide of formula $SOX_2$, wherein X is as previously defined, and reacting the product so formed with methanol.

* * * * *